US010300100B1

(12) United States Patent
Khalil et al.

(10) Patent No.: US 10,300,100 B1
(45) Date of Patent: May 28, 2019

(54) **EXTRACT OF *VICIA FABA* BEANS**

(71) Applicant: KING SAUD UNIVERSITY, Riyadh (SA)

(72) Inventors: Mutasim Ibrahim Khalil, Riyadh (SA); Mustafa Abdalla Mohamed Salih, Riyadh (SA); Ali Ahmed Mustafa Ali, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/145,090

(22) Filed: Sep. 27, 2018

(51) Int. Cl.
| | | |
|---|---|---|
| *A61K 36/48* | (2006.01) | |
| *A61K 31/513* | (2006.01) | |
| *A61K 31/196* | (2006.01) | |
| *A61K 31/047* | (2006.01) | |
| *A61K 31/16* | (2006.01) | |
| *A61K 31/198* | (2006.01) | |
| *A61K 31/167* | (2006.01) | |
| *A61K 31/522* | (2006.01) | |
| *A61K 31/428* | (2006.01) | |
| *A61P 25/08* | (2006.01) | |

(52) U.S. Cl.
CPC ............ *A61K 36/48* (2013.01); *A61K 31/047* (2013.01); *A61K 31/16* (2013.01); *A61K 31/167* (2013.01); *A61K 31/196* (2013.01); *A61K 31/198* (2013.01); *A61K 31/428* (2013.01); *A61K 31/513* (2013.01); *A61K 31/522* (2013.01); *A61P 25/08* (2018.01); *A61K 2236/10* (2013.01); *A61K 2236/331* (2013.01); *A61K 2236/333* (2013.01); *A61K 2236/35* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | |
|---|---|---|
| 2013/0195830 A1 | 1/2013 | Sipka et al. |
| 2015/0148305 A1 | 5/2015 | Ray, II et al. |
| 2015/0225423 A1 | 8/2015 | Attardo et al. |
| 2015/0306171 A1 | 10/2015 | Tran |

FOREIGN PATENT DOCUMENTS

| | | |
|---|---|---|
| CN | 102919466 A | 2/2013 |
| CN | 106668130 A | 5/2017 |
| JP | 60228420 A | 11/1985 |
| JP | 6222722 A | 1/1987 |

OTHER PUBLICATIONS

Salih et al., "A substance in broad beans (*Vicia faba*) is protective against experimentally induced convulsions in mice", Epilepsy & Behavior (2008) vol. 12, pp. 25-29.

Khalil et al., "Study of fatty acid composition, physiochemical properties and thermal stability of broad beans (*Vicia faba*) seed oil", Agric. Biol. J. N. Am. (2017), vol. 8, No. 4, pp. 141-146.

*Primary Examiner* — Susan Hoffman
(74) *Attorney, Agent, or Firm* — Richard C. Litman

(57) ABSTRACT

The extract of *Vicia faba* beans is prepared by soaking beans in distilled water overnight and then boiling in a water bath to reduce the volume of aqueous extract, which is then homogenized and filtered. The filtrate is concentrated to a smaller volume, lyophilized, and powdered. The lyophilized powder is extracted with hexane to remove oils and lipids. The oil-free lyophilized powder is dissolved in ethanol solvent and extracted for eight hours under reflux, and filtered. The volume of ethanol is reduced by a rotary evaporator, and a first off-white precipitate (sample A-1) is collected, washed with ethanol, and dried at 80° C. Mass spectrometry shows a molecular weight of 200.16447 g $mol^{-1}$, and an empirical formula of $C_9H_{16}N_2O_3$ is assigned. Intraperitoneal injection of mice with 50 mg/kg of A-1 twenty minutes prior to injection with strychnine protected the mice from strychnine-induced convulsions to the same extent as phenobarbitone (phenobarbital).

8 Claims, 7 Drawing Sheets

EXTRACT OF *VICIA FABA* BEANS

BACKGROUND

1. Field

The disclosure of the present patent application relates to anticonvulsant compounds of potential use in the treatment of epilepsy or avoidance of epileptic seizures, and particularly to an extract of *Vicia faba* beans, also known as broad beans, fava beans, or faba beans, and method of extracting the beans to obtain an anticonvulsant.

2. Description of the Related Art

The plant *Vicia faba*, also known as the broad bean, faba bean, fava bean, etc., is an ancient flowering plant long cultivated in and native to the Mediterranean region and southwestern Asia. It is a legume belonging to the Fabaceae bean family, having a broad, leathery pod and green fruit that mature to a blackish-brown color. *Vicia faba* can grow in cold and hot countries, withstanding harsh and cold climates, in soils with high salinity and a wide range of pH (4.5-8.3), as well as in clay soils.

Broad bean plants are highly susceptible to early summer infestations that can cause discoloration of pods, resulting in reduction of their economic value. These plants also are prone to bacterial and fungal diseases.

Several varieties of broad bean have been cultivated, and many modern varieties were developed for food use. *Vicia faba* is used for food for both humans and domestic animals, providing an important source of protein and fatty acids. Along with lentils, peas and chickpeas, *Vicia faba* are believed to be an important part of the eastern Mediterranean diet as early as 6000 BC or earlier, and still comprise a main dish for meals in the Middle East and the Nile region of Africa.

Fava beans are a common, important food in numerous African, Asian, Latin American, North American, and European countries. These beans are rich in dietary fiber, protein, phosphorus, copper, and manganese, and a very good source of folate. An intermediate value of α-tocopherol (17 ppm) that has the highest vitamin E activity was noted for broad beans. *Vicia faba* beans also contain antinutritional factors (i.e., substances that, when present in animal feed or water, tend to reduce the availability of one or more nutrients) that vary in concentration among the different varieties of VF. While used extensively as a food source, *Vicia faba* have also been documented to provide potential therapeutic benefits, including neuropharmacological effects.

*Vicia faba* beans are rich in tyramine, and also contain the alkaloids vicine and convicine. These alkaloids can induce hemolytic anemia in patients deficient in glucose-6-phosphate dehydrogenase (G6PD). The most frequent clinical manifestations are neonatal jaundice and acute hemolytic anemia.

Fava bean seedlings were also used as an initial source of L-DOPA (precursor to dopamine) to increase dopamine (DA) concentration in the treatment of Parkinson's disease. Ingestion of fava bean produces a significant increase in plasma L-DOPA, and urinary excretion of sodium and DA. Accordingly, fava beans may be helpful in treating conditions such as heart failure, liver cirrhosis, renal failure, and hypertension.

Epilepsy is a neurological disorder characterized by sudden, recurrent episodes of sensory disturbance, loss of consciousness, or convulsions (often referred to as seizures) associated with abnormal electrical activity in the brain. At least some epidemiological studies have noted a lower incidence of epilepsy in regions where fava beans are essentially a staple in the diet, which raises the possibility of one or more compounds in *Vicia faba* that may reduce the incidence, duration, or severity of epileptic seizures, including the convulsions associated therewith.

Thus, an extract of *Vicia faba* beans solving the aforementioned problems is desired.

SUMMARY

The extract of *Vicia faba* beans is prepared by soaking beans in distilled water overnight and then boiling in a water bath to reduce the volume of aqueous extract, which is then homogenized and filtered. The filtrate is concentrated to a smaller volume, lyophilized, and powdered. The lyophilized powder is extracted with hexane to remove oils and lipids. The oil-free lyophilized powder is dissolved in ethanol solvent and extracted for eight hours under reflux and filtered. The volume of ethanol is reduced by a rotary evaporator, and a first off-white precipitate (sample A-1) is collected, washed with a little ethanol, and dried at 80° C. Mass spectrometry shows a molecular weight of 200.16447 g $mol^{-1}$, and an empirical formula of $C_9H_{16}N_2O_3$ is assigned. Intraperitoneal injection of mice with 50 mg/kg of A-1 twenty minutes prior to injection with strychnine protected the mice from strychnine-induced convulsions to the same extent as phenobarbitone (phenobarbital).

Further extraction of the remaining ethanol solvent by column chromatography with a mixture of ammonium hydroxide, methanol, and ethanol extraction solvents produces a second off-white precipitate (sample A-2), which delays the onset of strychnine-induced convulsions, but is not as effective as sample A-1. Further isolation of compounds from the mixture of extraction solvents by GC-MS or HPLC-MS were performed, but did not include any further anticonvulsants of interest.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
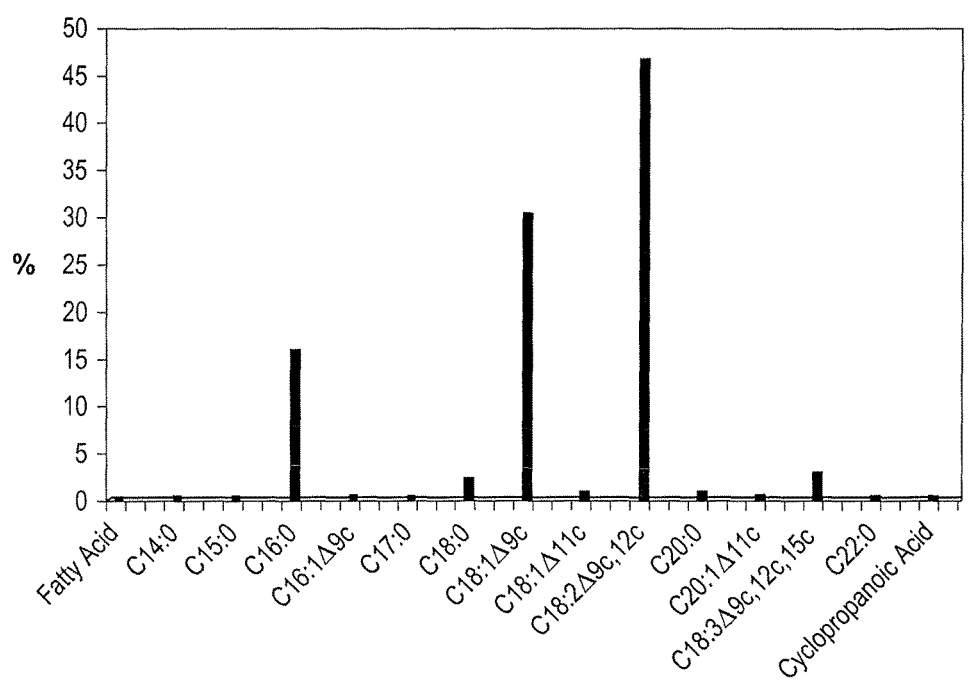
FIG. 1 is a histogram of fatty acids (%) extracted from a *Vicia faba* cultivar from Sudan.

The present work is an outgrowth of prior research conducted by two of the present inventors reported in M. A. M. Salih and A. A. Mustafa, "A substance in broad beans (*Vicia faba*) is protective against experimentally induced convulsions in mice", Epilepsy & Behavior, (2008), Vol. 12, pp. 25-29. As reported therein, the children in the school districts of Khartoum Province, Sudan experience a lower incidence of epilepsy than children of other countries or regions of the world. At the same time, *Vicia faba* beans (also known as broad beans, faba beans, or fava beans) are a staple in the diet of the school children of Khartoum, or of the Sudan generally. Our studies showed that aqueous extracts of *Vicia faba* beans, administered orally or in conjunction with an anticonvulsant (Diazepam), offered some protection from strychnine-induced convulsions. At the time, it was hypothesized that this may be due to the presence of a substance in fava beans intimately related to glycine. The present work attempts to isolate and identify any active ingredient(s) in fava beans that may inhibit or reduce convulsions incident to epileptic seizures as a potential active compound for a pharmaceutical treatment of epilepsy.

The extract of *Vicia faba* beans is prepared by soaking beans in distilled water overnight and then boiling in a water bath to reduce the volume of aqueous extract, which is then homogenized and filtered. The filtrate is concentrated to a smaller volume, lyophilized, and powdered. The lyophilized powder is extracted with hexane to remove oils and lipids. The oil-free lyophilized powder is dissolved in ethanol solvent and extracted for eight hours under reflux, and filtered. The volume of ethanol is reduced by a rotary evaporator, and a first off-white precipitate (sample A-1) is collected, washed with a little ethanol, and dried at 80° C. Mass spectrometry shows a molecular weight of 200.16447 g mol$^{-1}$, and an empirical formula of $C_9H_{16}N_2O_3$ is assigned. Intraperitoneal injection of mice with 50 mg/kg of A-1 twenty minutes prior to injection with strychnine protected the mice from strychnine-induced convulsions to the same extent as phenobarbitone (phenobarbital).

Further extraction of the remaining ethanol solvent by column chromatography with a mixture of ammonium hydroxide, methanol, and ethanol extraction solvents produces a second off-white precipitate (sample A-2), which delays the onset of strychnine-induced convulsions, but is not as effective as sample A-1. Further isolation of compounds from the mixture of extraction solvents by GC-MS or HPLC-MS were performed, but did not include any further anticonvulsants of interest.

The extract of *Vicia faba* beans will be better understood with reference to the following examples.

Example 1

Extraction of Samples for Analysis

Nine hundred grams of brown broad beans were soaked in 2.0 L of distilled water overnight, and then boiled in a water bath until the extract was reduced to 600 mL. The extract was homogenized and filtered. The filtrate was then concentrated to a volume of 100 mL, lyophilized, and powdered.

The lyophilized powder (50 g) was placed into a cellulose paper cone, and extracted with 600 mL hexane using a soxhlet extraction apparatus for 8 hours. The solvent was removed using a rotary vacuum distiller at 50° C., and then the residue was flushed with nitrogen to blanket the oil before storage (AOAC method 920.39). The lipid content was calculated from the weight of the oil (5.65 g), and the results were expressed as the lipid percentage of the original 900 g of beans—1.25%. See FIG. 1 and the analysis of fatty acid composition below.

The oil-free lyophilized powder was then extracted with ethanol, again using the above-mentioned procedure. The TLC results indicated a mixture of components.

Component A-1 was collected by partial precipitation, i.e., by filtering the refluxed mixture of oil-free lyophilized powder and ethanol and by removal of the ethanol solvent by the rotary evaporator, which left a first off-white precipitate, which was washed with ethanol and dried at 80° C. The extract sample A-1 was tested by FTIR and by mass spectrometry, as described below.

The remaining ethanol extract removed by the rotary evaporator and recovered by condensation of the solvent was further separated by column chromatography separation, where a portion of the ethanol extract was loaded onto a silica gel column chromatograph and carefully eluted using a mixture of solvents (5 ml NH$_4$OH (30%), 100 ml methanol, 900 ml ethanol) as a mobile phase that was gradually replaced with water. Many fractions (5-10 ml) were collected during the column chromatography, and the purity of each was tested using TLC (thin-layer chromatography. The TLC of fractions 10-13 indicated similar components, which were then collected. The solvent was driven off with a rotary evaporator, and the solid was dried at 80° C. A second off-white precipitate was collected by driving off the solvent from the chromatography column and designated sample extract A-2, which was tested by mass spectroscopy and $^1$H NMR, as described below. All other fractions were collected in one container, and the components were evaluated with GC-mass spectroscopy and HPLC, as described below.

Example 2

Analysis of Fatty Acid Composition

The fatty acids (oils) removed by the initial extraction of the lyophilized powder in hexane were analyzed as follows. The fatty acid methyl esters (FAME) composition was determined by converting the oil to fatty acid methyl esters. 200 µl lithium methoxide (2M) was added to a mixture of 40 mg of the oil in 1.0 ml n-hexane, followed by heating in a bath at 50° C. for few seconds. Then, 200 µl HCl (2N) is added. The major fatty acid components found in *Vicia faba* beans are palmitic acid (15.759%); stearic acid (2.16%) oleic acid (30.21%); linoleic acid (46.41%); and linolenic acid (2.74%). The remaining 2.7% comprises minor amounts of other fatty acids, as shown in the histogram of FIG. 1.

Example 3

Thin-Layer Chromatography

Thin-layer chromatography consisted of a stationary phase immobilized on a glass, and an organic solvent (55% phosphate buffer and 45% methanol). The constituents of a sample were identified by simultaneously running standards with the unknown. The bottom edge of the plate was placed in a solvent reservoir, and the solvent moved up the plate by capillary action. When the solvent front reached the other edge of the stationary phase, the plate was removed from the solvent reservoir. The separated spots were visualized with ultraviolet light or by placing the plate in iodine vapor. The different components in the mixture move up the plate at different rates due to differences in their partitioning behavior between the mobile liquid phase and the stationary phase. The TLC of the ethanol extract from the oil free lyophilized powder indicated a mixture of six components.

Example 4

Analysis of Sample Extract A-1

The FTIR spectrum of a dried portion of the ethanol extract indicated aromatic —CH at 3011 cm$^{-1}$, aliphatic —CH at 2926 and 2858 cm$^{-1}$, an —OH stretch at 3500 cm$^{-1}$, and carbonyl stretches at 1742 and 1643 cm$^{-1}$.

Figure 2:
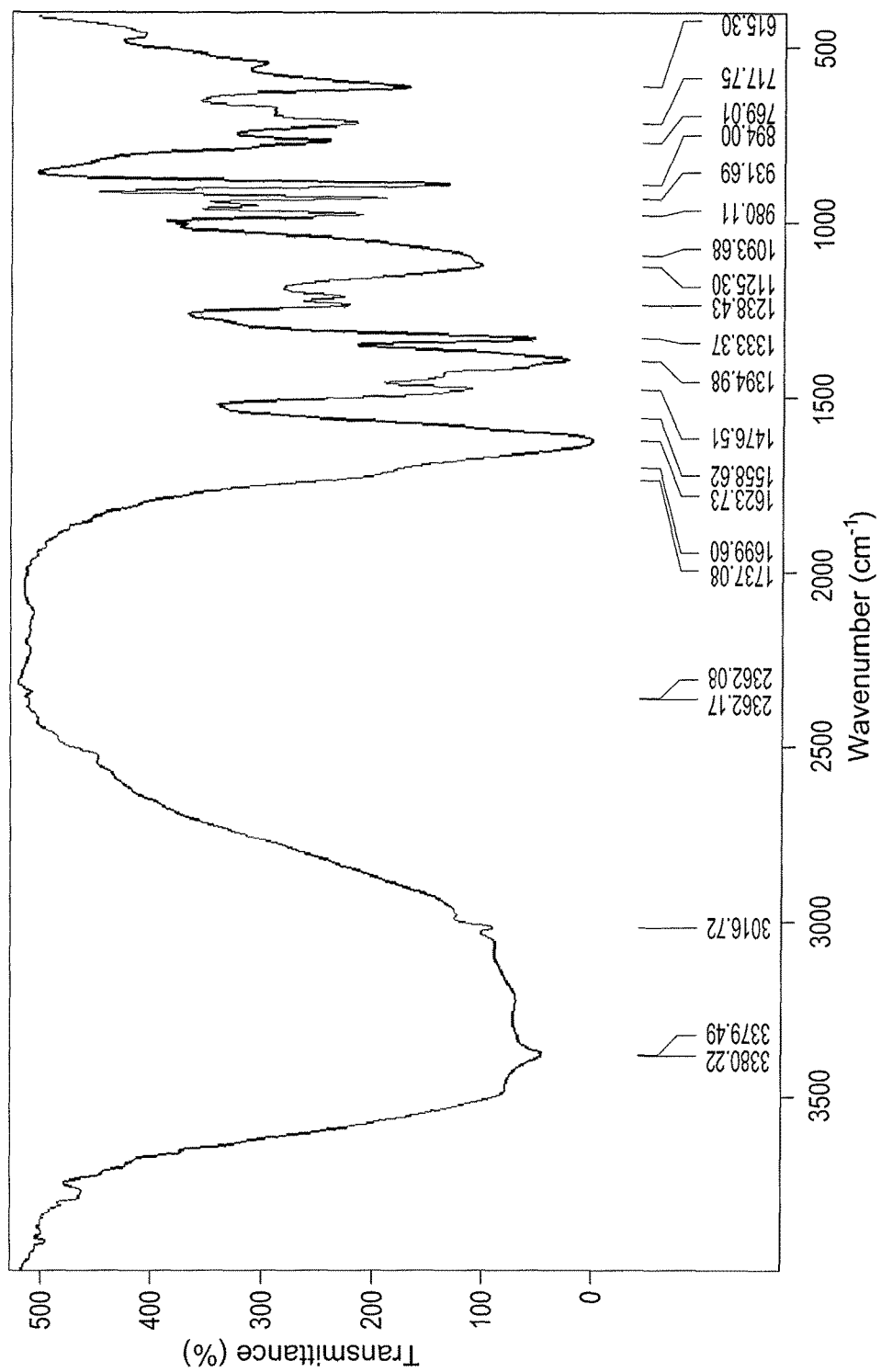
FIG. 2 is the FTIR spectrum of sample *Vicia faba* bean extract A-1.
Figure 3:
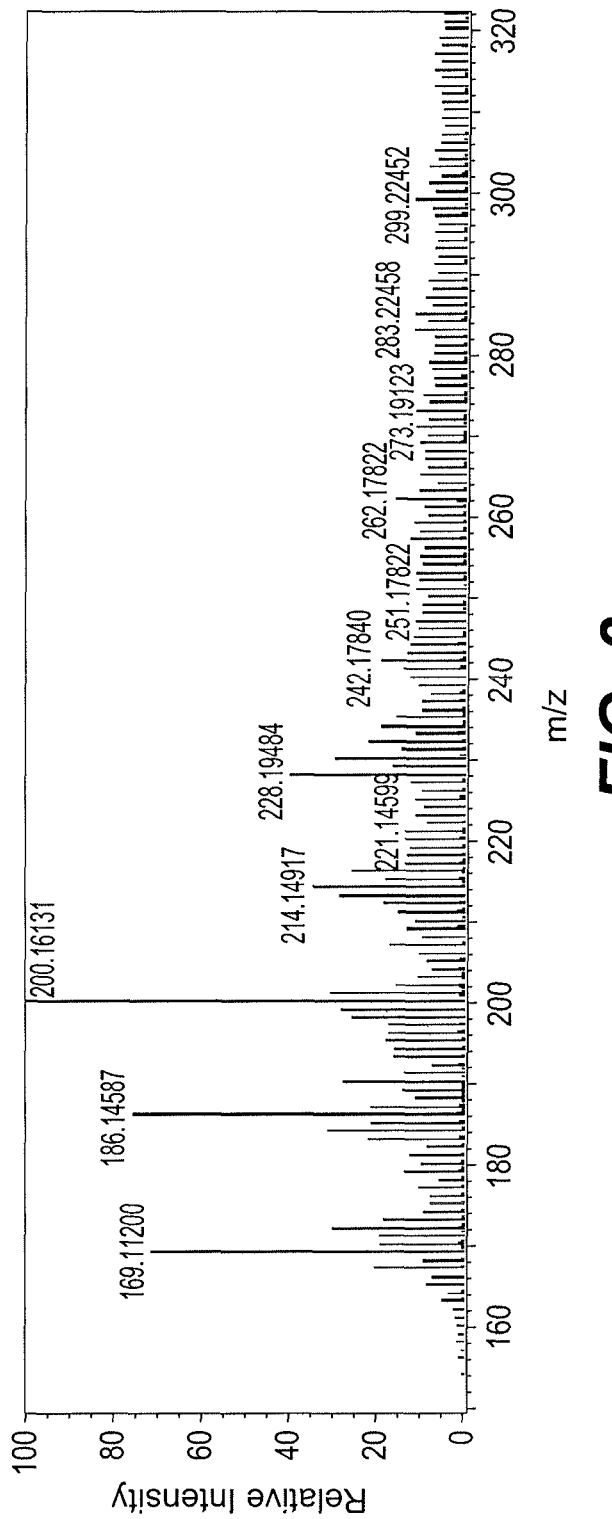
FIG. 3 is a mass spectrum of sample *Vicia faba* bean extract A-1.

The FTIR spectrum of the sample A-1 showed the persistence of the vibration bands at 3500, 2926, 2856 and 1742 cm$^{-1}$ with the disappearance of the band at 1643 cm$^{-1}$, indicating the presence of a mixture of carbonyl-containing components. See FIG. 2. The mass spectrum analysis indicates a molar mass of 200.16447 g·mol$^{-1}$, having two main fragmentations at m/z, 186.14587 and 169.11200 g/mol. See Table 1, and FIG. 3.

TABLE 1

Mass spectra data for sample extract A-1

| Mass | Intensity | Calculated mass | Mass difference (mmu) | Possible formula | Unsaturation number |
|---|---|---|---|---|---|
| 200.16447 | 3800990 | 200.16505 | -0.59 | $^{12}C_{11}{}^{1}H_{22}{}^{14}N_{1}{}^{16}O_{2}$ | 1.5 |
|  |  | 200.12867 | 35.80 | $^{12}C_{10}{}^{1}H_{18}{}^{14}N_{1}{}^{16}O_{2}$ | 2.5 |
|  |  | 200.11609 | 48.38 | $^{12}C_{9}{}^{1}H_{16}{}^{14}N_{2}{}^{16}O_{3}$ | 3.0 |

Two isomers that might be accurate based on the formula $C_9H_{16}N_2O_3$, and the fragmentation pattern observed in the GC-mass spectrum, are as follows. The first compound is 5,5-diethyl-6-hydroxy-1-methyldihydropyrimidine-2,4(1H,3H)-dione (compound 1) having the formula:

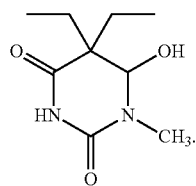

1

The second compound is 5,5-diethyl-6-methoxydihydropyrimidine-2,4(1H,3H)-dione (compound 2) having the formula:

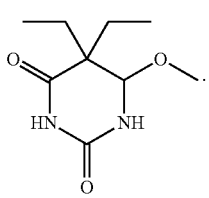

2

The 169.11200 g/mol fragment produced during MS, shown below as compound 3:

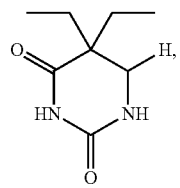

3 m/z = 169 can be produced from compound 1 by loss of the hydroxyl group from C6 and loss of a —CH$_2$ group from the methyl bonded to N1. It can also be produced from compound 2 by loss of the methoxy group bonded to C6.

The 186.14587 g/mol fragment produced during MS, shown below as compound 4:

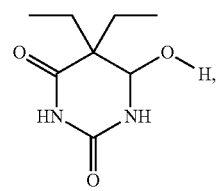

4 m/z = 186 can be produced from compound 1 by loss of a —CH$_2$ group from the methyl bonded to N1. It can also be produced from compound 2 by loss of a —CH$_2$ group from the methoxy group bonded to C6.

While sample extract A-1 may be either compound 1 or compound 2, it is also contemplated that sample extract A-1 may be a mixture of the two isomers having the same empirical formula.

Example 5

Analysis of Sample Extract A-2

Figure 4:
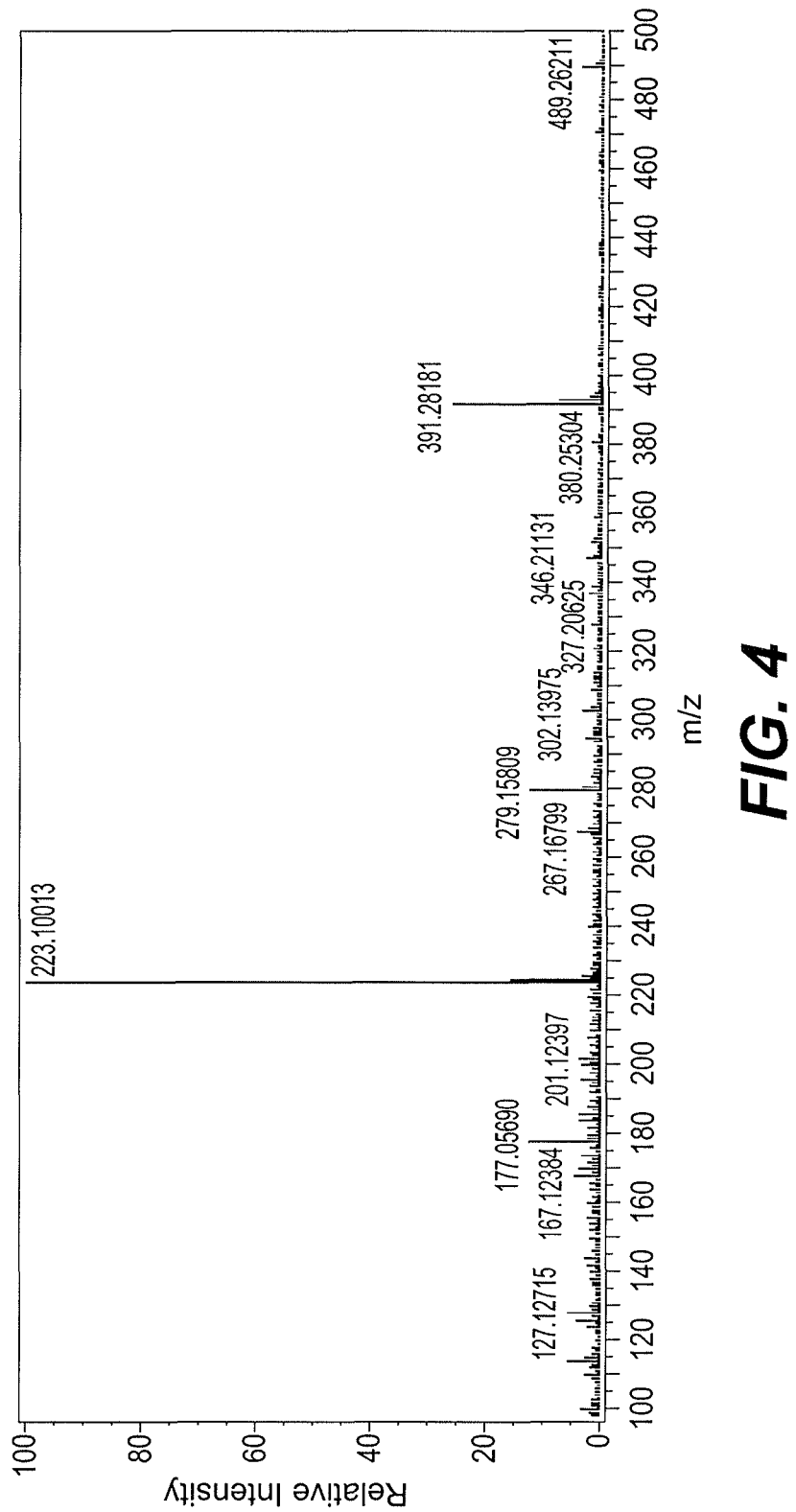
FIG. 4 is a mass spectrum of sample *Vicia faba* bean extract A-2.
Figure 5A:
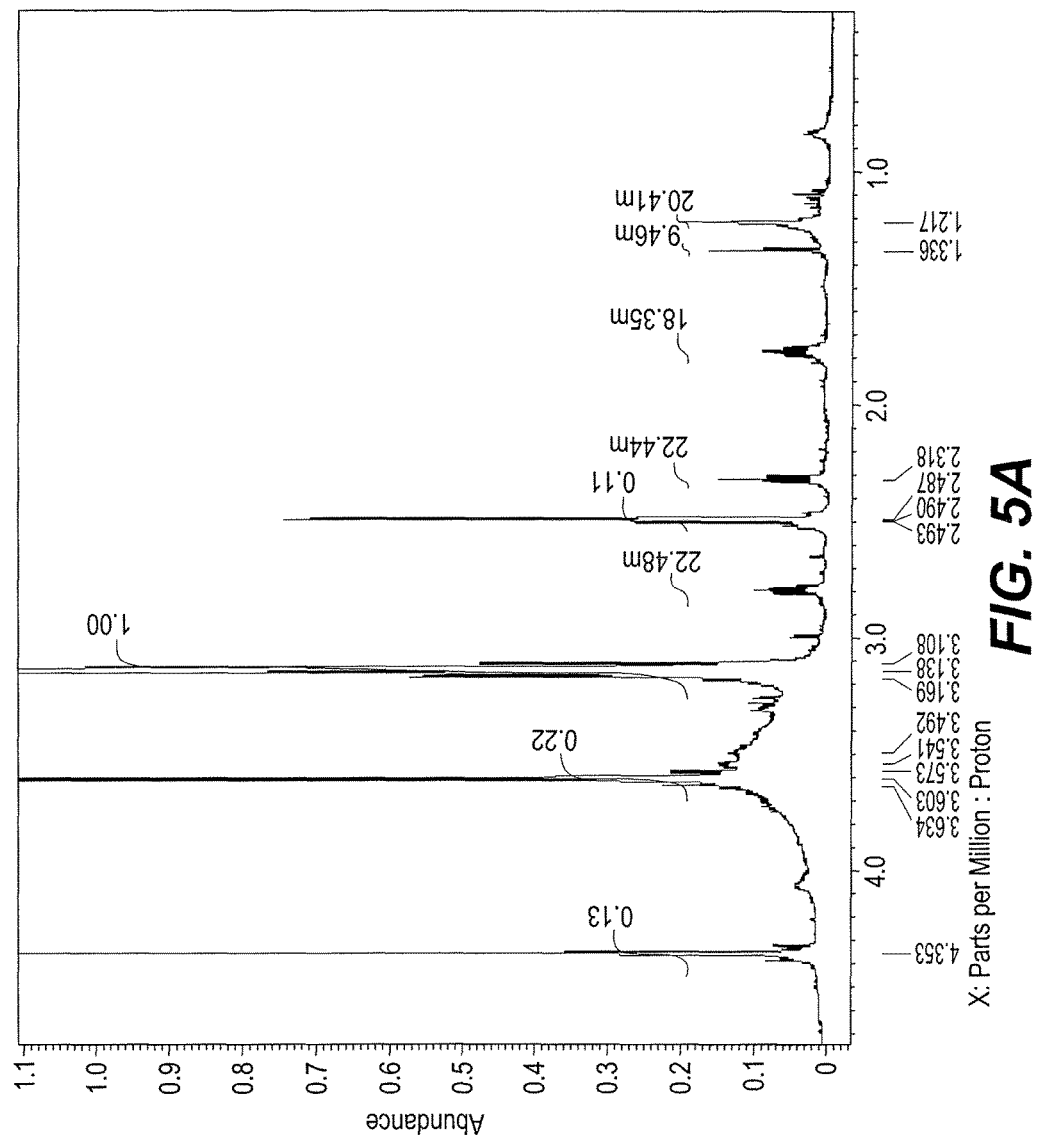
FIGS. 5A and 5B are two parts of the $^1$H-NMR spectrum of sample *Vicia faba* bean extract A-2.
Figure 5B:
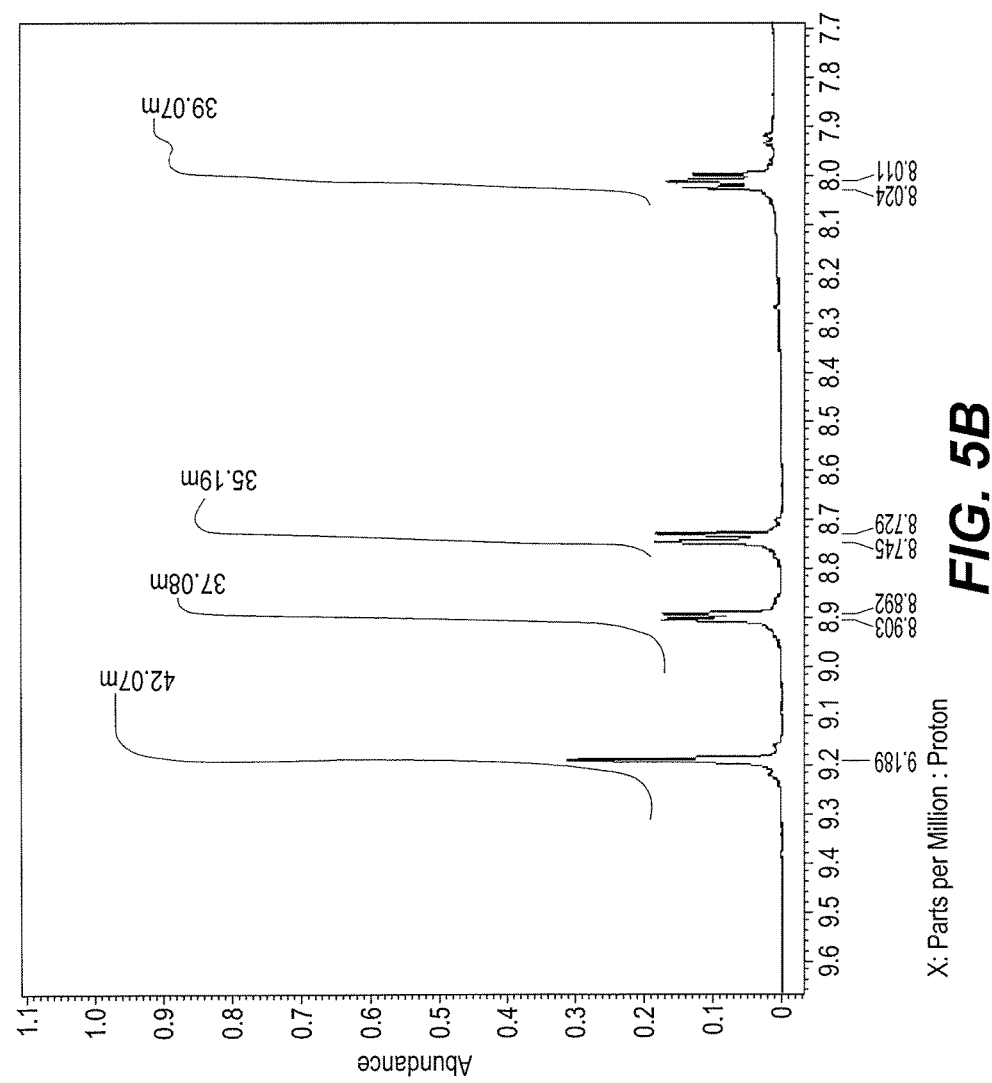

Sample extract A-2, which was obtained by column chromatography as described above in Example 1, was analysed by mass spectra and 1H NMR (see FIGS. 4, 5A, and 5B, and Table 2). The mass spectra of the component (A2) separated from the ethanol solution by column chromatography indicated a mass of 223.09703 g/mol, with a main fragment at m/z 177 g/mol.

TABLE 2

Mass spectra data for sample A-2

| mass | Calc. mass | Mass difference (m mu) | Possible formula |
|---|---|---|---|
| 223.09703 | 223.22522 | -128.19 | $C_{11}H_{13}NO_2$ |
|  | 223.2484 | -151.37 | $C_{11}H_{15}N_2O_3$ |
|  | 223.2053 | -108.31 | $C_{10}H_{11}N_2O_4$ |

An FTIR spectrum of sample extract A-2 shows the OH stretch at 3500 cm-1, the —NH stretch at 3080 cm-1, the =CH stretch at 3016 cm-1, and the methyl —CH stretch at 2987 cm-1. A carbonyl stretch is seen at 1737 cm-1 and the OCO stretch of carboxylate group at 1600 cm-1 region. The ¹H NMR spectrum, at FIGS. 5A and 5B, indicates phenolic protons. The most likely formulas are given in Table 2.

On the basis of the spectral data and the nitrogen rule, we expect that the formulation may be: $C_{11}H_{13}NO_4$, having a molar mass of 223.0 g/mol in accord with the GC-MS results. Compound 5 is the probable structure of this compound:

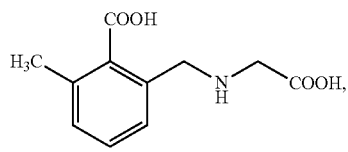

5 which may be named 2-(((carboxymethyl)amino)methyl)-6-methylbenzoic acid.

Example 6

Analysis of Other Identified Components

Figure 6:
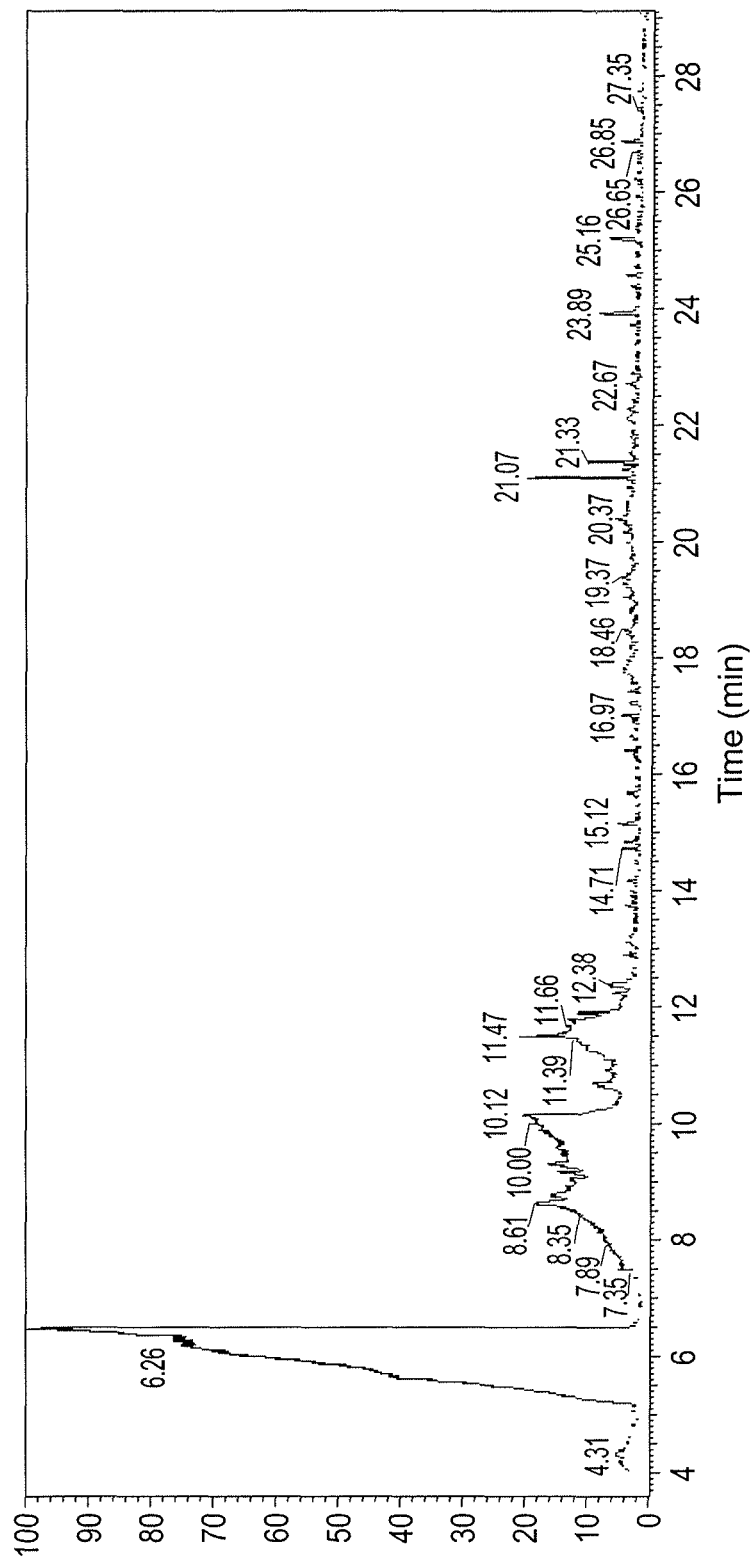
FIG. 6 is the mass spectrum of the ethanol extraction components from the *Vicia faba* cultivar remaining after separation and removal of the hexane extracts and extracts A-1 and A-2.

Other components in the fractions removed by column chromatography were identified by HPLC-GC-mass spectroscopy. See FIG. 6 and Table 3.

TABLE 3

Identification of other compounds

| No. | $t_R$ (min.) | Possible compound | M.W. | Formula |
|---|---|---|---|---|
| 6 | 6.46 | 2,3-Butanediol | 90 | $C_4H_{10}O_2$ |
| 7 | 10.12 | Butaneamide 3-N-dihydroxy | 119.12 | $C_4H_9NO_3$ |
| 8 | 11.47 | N,N-Dimethyl glycine | 103 | $C_4H_9NO_2$ |
| 9 | 21.07 | Lidocaine | 234 | $C_{14}H_{22}N_2O$ |
| 10 | 23.89 | 1,7-D imethylhypoxanthine | 164 | $C_7H_8N_4O$ |
| 11 | 25.16 | 2-Benzothiazolamine, N-methyl- | 164 | $C_8H_8N_2S$ |

The structures of the other identified compounds are shown below.

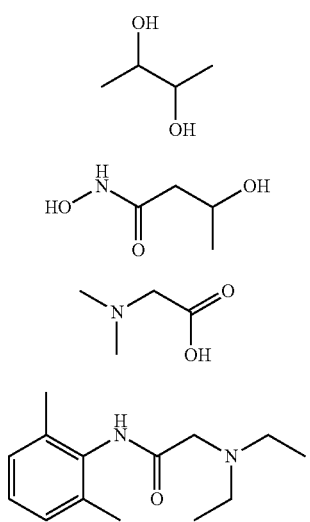

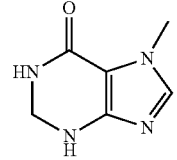

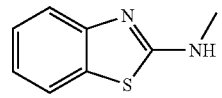

While present in the extracts, compounds 6 through 11 did not contribute to anticonvulsant activity, with the possible exception of compound 8 (N,N-dimethyl glycine).

Example 7

Testing for Anticonvulsant Activity

BALB/c mice (25-30 g) were used throughout the study. The mice were deprived of solid food for 18 hours prior to the experiment. They were kept in wire-mesh cages to prevent cropophagia, and they were allowed water ad libitum. All research was conducted in accordance with internationally-accepted principles for laboratory animal use and care.

Three hundred grams of brown broad beans were soaked in 1.0 L of distilled water overnight and boiled in a water bath until the extract was reduced to 300 mL (about 3 hours). The extract was homogenized and filtered. The filtrate was concentrated by cold evaporation to a volume of 50 mL. This treatment resembles the way in which broad beans are cooked for a meal in Sudan. The filtrate was then lyophilized and powdered, and the oils or lipids were removed from the lyophilized powder by extraction in hexane in a Soxhlet extractor, as described in Example 1.

The chemical components of the oil-free lyophilized broad beans powder were extracted with ethanol. To 50 g of the powder, 200 ml of pure ethanol were added, and the mixture was refluxed for 8 hours. The mixture was then filtered, and the ethanol solution was concentrated to approximately 50 ml by rotary pump. The off-white precipitate was separated out, filtered, and washed with ethanol and dried.

The mice were pretreated orally with the extract (at a dose of 0.01 mL/g of mouse) and divided into two groups of 12 mice each. Then, at 30 minutes after pretreatment, the two groups were injected intraperitoneally (IP) with strychnine, one group at 0.112 mg/kg, and the other group at 0.225 mg/kg. The numbers of animals that died after treatment with extract and strychnine were recorded and compared with the numbers of control mice (two groups, 12 mice each) that had received the same doses of strychnine only.

Statistics were analyzed using SPSS (Version 12.0). Paired t test (two tailed), Fisher's exact test, ANOVA, and multiple regression analysis to compare data among the different groups. A P value <0.05 was considered to indicate significance.

The control experiments were conducted where Strychnine (0.225 mg/kg) was injected intraperitoneally in a group of 12 mice. The mice started convulsions almost immediately, and all died within 2.5 minutes following the injection of strychnine. See Table 4.

TABLE 4

Control - Strychnine (0.45 mg/kg, intraperitoneally)

| No. | Behavior before convulsions | Time To DEATH (minutes) |
|---|---|---|
| 1 | Writhing | 3 |
| 2 | Writhing | 3 |
| 3 | Writhing | 2 |
| 4 | Writhing | 2 |
| 5 | Writhing | 2 |
| 6 | Writhing | 2.2 |
| 7 | Writhing | 2 |
| 8 | Writhing | 2 |
| 9 | Writhing | 2.1 |
| 10 | Writhing | 2.3 |
|  | mean | 2.3 ± 0.26 |

When phenobarbitone (phenobarbital) (50 mg/kg) was injected intraperitoneally 15 minutes before strychnine, it protected against the strychnine-induced convulsions, completely. See Table 5.

TABLE 5

Phenobarbitone (50 mg/kg., i.p.) + Strychnine (0.45 mg/kg, i.p.)

| No. | Time to first convulsion (minutes) | Survival recovered time after strychnine injection (minutes) |
|---|---|---|
| 1 | 7 | 70 |
| 2 | 8 | 80 |
| 3 | 5 | 80 |
| 4 | 7 | 90 |
| 5 | 6.5 | 70 |
| 6 | 7 | 75 |
| 7 | 8 | 80 |
| 8 | 9 | 75 |
| 9 | 9 | 70 |
| 10 | 10 | 75 |
|  | mean | 76.5 ± 5.58 minutes |

Compound A-1, injected intraperitoneally in a dose of 50 mg/kg, protected mice against the strychnine-induced convulsions completely, or at least as effectively as the phenobarbitone in protecting mice against the strychnine-induced convulsions. See Table 6.

TABLE 6

Effect of sample A-1 (50 mg/kg i.p.) on seizures induced by strychnine (0.225 mg/kg i.p.)

| No. | Behavior before convulsions | Survival recorded time after strychnine injection (minutes) |
|---|---|---|
| 1 | Writhing | 90 |
| 2 | Writhing | 52 |
| 3 | Writhing | 55 |
| 4 | Writhing | 60 |
| 5 | Writhing | 70 |
| 6 | Writhing | 60 |
| 7 | Writhing | 70 |
| 8 | Writhing | 60 |
| 9 | Writhing | 75 |
| 10 | Writhing | 70 |
|  |  | Mean = 60.2 ± 7.2 |

Compound A-2, in contrast, produced slight but incomplete protection against the strychnine-induced convulsions, protecting the mice only for an average of 12.5 minutes. See Table 7 and Table 8.

TABLE 7

Effect of sample A-2 (50 mg/kg i.p.) on seizures/time to death induced by strychnine (0.45 mg/kg i.p.)

| No. | Time to first convulsion | Survival time recorded after strychnine injection (minutes) |
|---|---|---|
| 1 | 7.5 | 13 |
| 2 | 7.5 | 9.5 |
| 3 | 5 | 8 |
| 4 | 6 | 7.5 |
| 5 | 6.5 | 18 |
| 6 | 6.5 | 17 |
| 7 | 5.5 | 12 |
| 8 | 6.5 | 14 |
| 9 | 7.5 | 10 |
| 10 | 8 | 15 |
|  |  | Mean = 12.4 ± 0.25 |

TABLE 8

Effect of sample extract dosage on strychnine-induced (0.45 mg/kg, i.p.) convulsions in mice

| Dose of purified compound (mg/kg, i.p.) | Survival recorded time after strychnine injection (minutes) | Remarks |
|---|---|---|
| Sample extract A-1 | | |
| 10 | 43.2 ± 5.1 | No death recorded |
| 25 | 55.7 ± 6.3 | No death recorded |
| 50 | 60.2 ± 7.2 | No death recorded |
| Sample extract A-2 | | |
| 10 | 2.5 ± 0.19 | Writhing followed by death |
| 25 | 7.6 ± 0.56 | Writhing followed by death |
| 50 | 12.4 ± 0.25 | Writhing followed by death |

It would therefore appear that the extract of *Vicia faba* beans, labelled herein as sample A-1, may be effective in inhibiting the occurrence or modifying the severity of seizures and convulsions incident to epilepsy.

It is to be understood that the extract of *Vicia faba* beans is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of producing an anticonvulsant extract of *Vicia faba* beans, comprising the steps of:
   extracting *Vicia faba* beans in water to obtain an aqueous extract;
   lyophilizing the aqueous extract and powdering the lyophilized aqueous extract to obtain a lyophilized powder;
   extracting the lyophilized powder in hexane to remove lipids and obtain an oil-free lyophilized powder;
   extracting the oil-free lyophilized powder in ethanol solvent under reflux and filtering off the ethanol solvent;
   removing the ethanol solvent by rotary evaporator to leave a precipitate;
   washing the precipitate in ethanol; and
   drying the precipitate at 80° C.

2. The method of producing an anticonvulsant extract of *Vicia faba* beans according to claim 1, wherein the *Vicia faba* beans are a cultivar of the Sudan.

3. The method of producing an anticonvulsant extract of *Vicia faba* beans according to claim 1, wherein the step of extracting *Vicia faba* beans in water comprises the steps of:
   soaking the beans in distilled water overnight to obtain the aqueous extract;
   boiling the water-soaked beans in a water bath until the aqueous extract is reduced in volume by at least two-thirds;
   homogenizing the aqueous extract; and
   filtering the homogenized aqueous extract, retaining the filtrate.

4. The method of producing an anticonvulsant extract of *Vicia faba* beans according to claim 3, wherein the step of lyophilizing the aqueous extract comprises lyophilizing the filtrate.

5. The method of producing an anticonvulsant extract of *Vicia faba* beans according to claim 1, wherein the step of extracting the lyophilized powder in hexane comprises extracting the lyophilized powder in hexane in a Soxhlet extractor.

6. The method of producing an anticonvulsant extract of *Vicia faba* beans according to claim 1, wherein the step of extracting the oil-free lyophilized powder in ethanol solvent under reflux comprises heating the oil-free lyophilized powder in ethanol solvent under reflux for about eight hours.

7. The method of producing an anticonvulsant extract of *Vicia faba* beans according to claim 1, wherein the dried precipitate has a molar mass of 200.16447 g/mol.

8. The method of producing an anticonvulsant extract of *Vicia faba* beans according to claim 1, wherein the dried precipitate has an empirical formula of $C_9H_{16}N_2O_3$.

\* \* \* \* \*